United States Patent

Kogure et al.

Patent Number: 5,196,487
Date of Patent: Mar. 23, 1993

[54] CORROSION PREVENTIVE RESIN AND PHOTOPOLYMERIZABLE COMPOSITION INCORPORATING SAME

[75] Inventors: Hideo Kogure, Atsugi; Heihachi Murase, Kanagawa; Naozumi Iwasawa, Hiratsuka, all of Japan

[73] Assignee: Kansai Paint Company, Limited, Hyogo, Japan

[21] Appl. No.: 712,279

[22] Filed: Jun. 10, 1991

[30] Foreign Application Priority Data

Jun. 12, 1990 [JP] Japan .................. 2-154356
Aug. 9, 1990 [JP] Japan .................. 2-212299

[51] Int. Cl.$^5$ .................. C08F 2/46; C08F 3/34; C08J 3/28; C08C 19/20
[52] U.S. Cl. .................. 525/343; 522/90; 522/99; 522/100; 522/149; 524/547; 525/291; 526/286
[58] Field of Search .................. 522/90, 99, 100, 149; 524/547; 525/291, 343; 526/286

[56] References Cited

U.S. PATENT DOCUMENTS 3,265,673 8/1966 Richards et al. .................. 526/286
4,605,590 8/1986 Delseth et al. .................. 525/343

Primary Examiner—Paul R. Michl
Assistant Examiner—Peter Szekely
Attorney, Agent, or Firm—Armstrong, Westerman, Hattori, McLeland & Naughton

[57] ABSTRACT

A corrosion preventive resin having in the molecule at least one chelate forming group selected from among groups represented by the formula

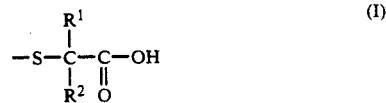

wherein $R^1$ and $R^2$ are the same or different and are each a hydrogen atom or alkyl having 1 to 8 carbon atoms, and groups represented by teh general formula

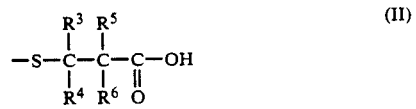

wherein $R^3$, $R^4$, $R^5$ and $R^6$ are the same or different and are each a hydrogen atom, alkyl having 1 to 8 carbon atoms or a group forming a bivalent o-phenylene group along with two carbon atoms attached thereto. A photopolymerizable composition which includes (a) a resin having in the molecule at least one mole of polymerizable double bond per 1000 g of the resin and having per molecule at least one chelate forming group selected from among the groups represented by formula (II) and formula (III), and (b) a photopolymerization initiator is also disclosed.

10 Claims, No Drawings

CORROSION PREVENTIVE RESIN AND PHOTOPOLYMERIZABLE COMPOSITION INCORPORATING SAME

The present invention relates to a resin for forming a tough metal chelate complex on the surface of metal to prevent the corrosion of the metal and to a photopolymerizable composition incorporating the resin.

Usually, metals are prevented from corrosion, for example, by treating the surface of metal, i.e., by forming an inorganic coating of phosphoric acid salt, chromic acid salt or the like over the metal surface, or by techniques for forming corrosion preventive coatings, i.e., by forming an organic coating of epoxy resin, phenol resin or the like over the metal surface.

However, the treatment of metal surfaces has the drawback of causing environmental pollution due to liquid wastes containing heavy metals, using extremely poisonous chemicals such as acids, alkalis or cyano-containing compounds, and necessitating a complex process.

Corrosion preventive coatings have the problem that the bond strength between the coating and the metal is insufficient to completely prevent the corrosion reaction.

Accordingly, corrosion preventive techniques still remain to be established which are free of pollution, practically useful and excellent in corrosion preventing effects, and it has been desired to develop such techniques.

An object of the present invention is to provide a novel corrosion preventive resin having an outstanding corrosion preventing effect and a photopolymerizable composition having the resin incorporated therein.

Another object of the invention is to provide a novel corrosion preventive resin which is usable as a pollution-free surface treating agent in place of inorganic surface treating agents such as phosphoric acid salts and chromic acid salts and which is more excellent than epoxy resins, phenol resins, etc. in corrosion preventing effect, and a photopolymerizable composition having the resin incorporated therein.

These and other objects of the present invention will become apparent from the following description.

The present invention provides a corrosion preventive resin characterized in that the resin has in the molecule at least one chelate forming group selected from among groups represented by the general formula

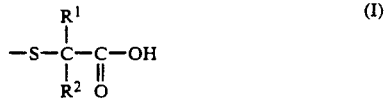

wherein $R^1$ and $R^2$ are the same or different and are each a hydrogen atom or alkyl having 1 to 8 carbon atoms, and groups represented by the general formula

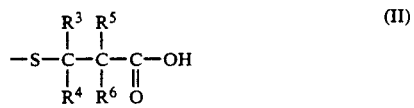

wherein $R^3$, $R^4$, $R^5$ and $R^6$ are the same or different and are each a hydrogen atom, alkyl having 1 to 8 carbon atoms or a group forming a bivalent o-phenylene group along with two carbon atoms attached thereto.

The present invention also provides a photopolymerizable composition characterized in that the composition consists essentially of (a) a resin having in the molecule at least one mole of polymerizable double bond per 1000 g of the resin and having per molecule at least one chelate forming group selected from among the groups represented by the general formula (I) and the groups represented by the general formula (II), and (b) a photopolymerization initiator.

In view of the foregoing situation of the prior art, we have conducted intensive research from the viewpoint of surface chemistry, thermodynamics, electrochemistry, complex chemistry, etc. to develop a resin having excellent corrosion preventing properties and obtained the following novel findings.

(1) High-molecular-weight compounds capable of forming a chelate complex bond to metals much more firmly than epoxy resins, phenol resins and like resins. Especially when such a high-molecular-weight compound has a chelate forming group comprising a thioether group and a carboxyl group attached thereto with an intervening carbon atom, the chelate formed gives energy to bond the compound to the metal which energy is greater than the energy of corrosion reaction.

(2) The high-molecular-weight compound having the specific chelate forming group mentioned serves to neutralize the charge of metal ions.

(3) When the high-molecular-weight compound further has a polymerizable double bond incorporated therein and is used in combination with a photopolymerization initiator, the composition obtained can be rapidly cured with light and achieves exceedingly high productivity.

The present invention has been accomplished based on these novel findings.

It is required that the resin of the present invention have at least one of the chelate forming groups represented by the formulae (I) and (II).

Typical examples of chelate forming groups represented by the formulae (I) and (II) are

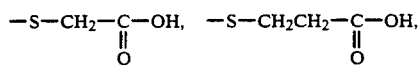

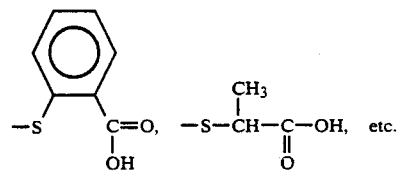

The chelate forming group of the resin of the invention is a portion which forms a chelate complex having a stable five-membered ring (in the case of the chelate forming group of the formula (I)) or six-membered ring (in the case of the chelate forming group of the formula (II)) of the intramolecular complex with a positive bivalent or trivalent metal ion. Models of chelate complexes to be formed are given below wherein the chelate forming groups is represented by

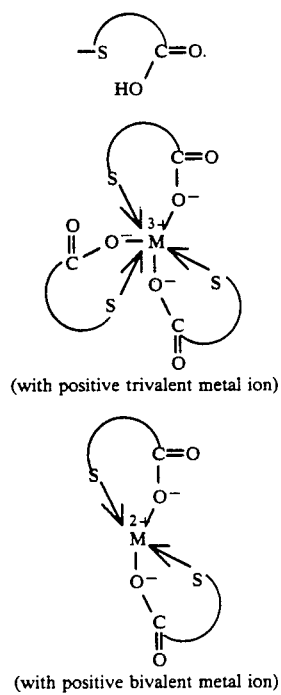

(with positive trivalent metal ion)

(with positive bivalent metal ion)

Thus, three chelate forming groups combine with a positive trivalent metal ion or two chelate forming groups combine with a positive bivalent metal ion to form a chelate complex of five-membered ring or six-membered ring wherein the charge of the metal ion is neutralized with carboxylate ions. Since the chelate complex is formed with the charge neutralized, the resin is resistant to the flow of corrosion current which causes corrosion to metal. Furthermore, the complex is in the form of a five- or six-membered ring and is therefore structurally stable. Presence of more than two intervening carbon atoms is not desirable because the resulting complex has a ring of 7 or more members to exhibit lower stability.

According to the invention, it is required that the chelate forming group be combined with the base portion of the resin by a thioether bond.

For example, the following methods (1) to (4) can be used for preparing the resin of the invention wherein the chelate forming group is combined with the base portion of the resin by a thioether bond.

(1) A method wherein a polymerizable double bond is introduced into a terminal position or side chain of a resin, and a compound represented by the formula (III) or (IV) below is attached to the double bond by an addition reaction.

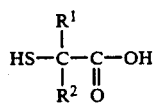 (III)

wherein $R^1$ and $R^2$ are as defined above.

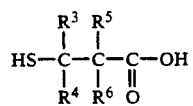 (IV)

wherein $R^3$, $R^4$, $R^5$ and $R^6$ are as defined above.

(2) A method wherein the addition reaction product of a compound having both a polymerizable double bond and a first functional group, such as hydroxyl group, with a compound represented by the formula (III) or (IV) is reacted with a compound or resin having a second functional group, such as isocyanate group, which is reactive with the hydroxyl or like first functional group of the product.

(3) A method wherein a compound having a chelate forming group of the formula (I) or (II) and a polymerizable double bond is copolymerized with other polymerizable unsaturated monomer.

(4) A method wherein a compound represented by the formula (III) or (IV) and a silane compound or resin having an etherified silanol group and a polymerizable double bond are subjected to an addition reaction, or a method wherein the compound or resin obtained by this method and having a structural portion of the formula (I) or (II) and the etherified silanol group is subjected to partial condensation, or to partial copolycondensation along with other silane compound having an etherified silanol group.

The resin having a polymerizable double bond at a terminal position or side chain for use in the method (1) is not limited specifically but can be any of various resins obtained by known methods. Such a resin can be prepared, for example, from a resin having an epoxy group at a terminal position or side chain (such as a copolymer of glycidyl (meth)acrylate, allyl glycidyl ether or like epoxy-containing polymerizable unsaturated monomer and other polymerizable monomer, or bisphenol-type or like epoxy resin), by adding (meth)acrylic acid or like carboxyl-containing polymerizable unsaturated compound to the resin to open the epoxy group for the introduction of a polymerizable unsaturated group into the resin. This addition reaction can be accomplished, for example, by heating the two reactants at about 50° to about 150° C. for about 30 minutes to about 8 hours in the presence or absence of a catalyst such as a quaternary ammonium salt.

Alternatively, an isocyanate compound containing a polymerizable unsaturated group, such as isocyanato ethyl (meth)acrylate, m-isopropenylphenyl isocyanate or m-isopropenyl-α, α-dimethylbenzyl isocyanate, can be added to the hydroxyl group of a resin having a hydroxyl group, such as acrylic resin, polyester resin, alkyd resin or epoxy resin, whereby the polymerizable unsaturated group can be introduced into the resin. This addition reaction can be effected, for example, by reacting the resin and the compound at 20° to 100° C. for about 1 to about 10 hours in the presence or absence of a tin catalyst such as dibutyltin octylate.

The resin having a polymerizable double bond at the terminal position or side chain and thus obtained is reacted with a compound of the formula (III) or (IV), whereby the chelate forming group represented by the formula (I) or (II) is introduced into the resin. Typical of compounds represented by the formula (III) or (IV) are, for example, thiosalicylic acid, thioglycollic acid, 3-mercaptopropionic acid, 2-mercaptopropionic acid and the like. Among these, thiosalicylic acid is desirable since this acid smells less and easy to handle. This addition reaction of the compound of the formula (III) or (IV) with the polymerizable double bond of the resin can be conducted usually at about 20° to about 100° C. for about 1 to about 24 hours, for example, in the presence or absence of an amine catalyst.

The method (2) is the method (1) as practiced in a different order of reactions. The reaction product having a chelate forming group of the formula (I) or (II) and the first functional group is prepared first, and the first functional group of the product is then reacted with the second functional group of a compound or resin to increase the molecular weight of the reaction product.

The compound having a chelate forming group of the formula (I) or (II) and a polymerizable double bond for use in the method (3) can be obtained, for example, by preparing an addition reaction product of a compound of the formula (III) or (IV) with a hydroxyl-containing unsaturated monomer, such as 2-hydroxylethyl (meth)acrylate, and adding the hydroxyl group of the product to a polymerizable double bond-containing monoisocyanate compound such as isocyanato ethyl (meth)acrylate, m-isopropenylphenyl isocyanate or m-isopropenyl-α, α-dimethylbenzyl isocyanate. The reaction of the compound of the formula (III) or (IV) with the hydroxyl-containing unsaturated monomer is carried out, for example, at about 20° to about 100° C. for about 1 to about 24 hours in the presence or absence of an amine catalyst using the two reactants in equimolar amounts. The resulting product has a hydroxyl group, which is added to the monoisocyanate compound having a polymerizable double bond by a reaction conducted, for example, at about 20° to about 100° C. for about 1 to about 10 hours in the presence of a tin catalyst using the two reactants in equimolar amounts. The compound having a chelate forming group of the formula (I) or (II) and a polymerizable double bond can be obtained alternatively by a method other than the above, for example, by reacting 2 moles of a compound represented by the formula (III) or (IV) with 2 moles of a hydrocarbon halide having a polymerizable double bond, such as allyl bromide, in the presence of 1 mole of a complex-forming metal salt, such as nickel chloride, and washing the precipitate obtained with an acid.

Examples of other polymerizable unsaturated monomers for use in copolymerization with the compound having a chelate forming group of the formula (I) or (II) and a polymerizable double bond in the method (3) are $C_1$ to $C_{18}$ alkyl esters of (meth)acrylic acid such as methyl (meth)acrylate, ethyl (meth)acrylate, n-butyl (meth)acrylate, isobutyl (meth)acrylate, hexyl (meth)acrylate, 2-ethylhexyl (meth)acrylate and lauryl (meth)acrylate; $C_2$ to $C_8$ hydroxyalkyl esters of (meth)acrylate such as 2-hydroxyethyl (meth)acrylate and hydroxypropyl (meth)acrylate; hydroxyl-containing unsaturated monomers such as allyl alcohol; acid group-containing unsaturated monomers such as (meth)acrylic acid, crotonic acid and itaconic acid; aromatic vinyl compounds such as styrene, α-methylstyrene and vinyltoluene; and other monomers such as vinyl acetate, (meth)acrylamide, (meth)acrylonitrile and N-methylol (meth)acrylamide butyl ether. These monomers can be used singly, or at least two of them are usable in combination.

The copolymerization of the compound having a chelate forming group of the formula [I] or [II] and a polymerizable double bond with the above other polymerizable unsaturated monomer is conducted by a known method per se, for example, by heating the two components in the presence of a polymerization catalyst, and preferably in the presence of an organic solvent.

Examples of preferred silane compounds or resins having a polymerizable double bond and an etherified silanol group for use in the method (4) are silane compounds represented by the formula (V) given below, resins prepared by subjecting one or at least two of such silane compounds to partial condensation, and partial copolycondensation products prepared from such a silane compound and other silane compound having etherified silanol groups

wherein A is an unsaturated hydrocarbon group or unsaturated carbonyloxyalkyl group, X is a hydrogen atom, hydrocarbon group having 1 to 18 carbon atoms, alkoxyl group having 1 to 18 carbon atoms, aryloxy group having 6 to 8 carbon atoms or alicyclic hydrocarbonoxy group having 5 to 8 carbon atoms, and Y and Z are the same or different, may be the same as X and are each an alkoxyl group having 1 to 18 carbon atoms, aryloxy group having 6 to 8 carbon atoms or alicyclic hydrocarbonoxy group having 5 to 8 carbon atoms.

Examples of preferred groups A are vinyl, allyl, methacryloyloxyethyl, acryloyloxyethyl, methacryloyloxypropyl, acryloyloxypropyl and like groups.

Among the alkoxy groups having 1 to 18 carbon atoms, aryloxy groups having 6 to 8 carbon atoms and alicyclic hydrocarbonoxy groups having 5 to 8 carbon atoms represented by X, Y and Z, preferable examples are methoxy, ethoxy, propoxy, butoxy, hexoxy, octoxy, methoxyethoxy and like alkoxy groups having 1 to 8 carbon atoms, phenoxy group, cyclohexyloxy group and the like.

Preferable among the hydrocarbon groups represented by X and having 1 to 18 carbon atoms are methyl, ethyl, n-propyl, isopropyl, n-butyl, n-hexyl and like alkyl groups having 1 to 6 carbon atoms; phenyl, methylphenyl, ethylphenyl and like aryl groups having 6 to 8 carbon atoms; and cyclopentyl, cyclohexyl and like alicyclic hydrocarbon groups having 5 to 8 carbon atoms.

Typical examples of silane compounds represented by the formula (V) are vinyltrimethoxysilane, vinyltriethoxysilane, vinyltris(n-propoxy)silane, vinylbis(methoxy)methylsilane, vinylbis(ethoxy)methylsilane, vinylbis(n-propoxy)methylsilane, allyltrimethoxysilane, β-oyloxyethyltrimethoxysilane, β-methacryloyloxyethylacryltrimethoxysilane, γ-acryloyloxypropyltrimethoxysilane, γ-methacryloyloxypropyltrimethoxysilane, γ-methacryloyloxypropyl(methyldiethoxy)silane, β-methaozyloyloxyethyltriethoxysilane, γ-methacryloyloxypropyltriethoxysilane, γ-methacryloyloxypropyltris(2-methoxyethoxy)silane, β-methacryloyloxypropyltris(n-buloxy)silane, γ-methacryloyloxypropyltris(isobutoxy)silane, γ-methacryloyloxypropyltris(isopropoxy)silane, etc.

The above-mentioned other silane compound which has etherified silanol groups and which can be subjected to partial copolycondensation with a silane compound represented by the formula (V) is a silane compound having at least two etherified silanol groups. Examples of such compounds are methyltrimethoxysilane, methyltriethoxysilane, phenyltrimethoxysilane, phenyltriethoxysilane, isobutyltrimethoxysilane, isobutyltriethoxysilane, ethyltrimethoxysilane, dimethyldimethoxysilane, diphenyldimethoxysilane, diphenyldiethoxysilane, diisobutyldimethoxysilane, diisobutyldipropoxysilane and like silane compounds, and partial polycondensation products of these silane compounds.

The partial condensation of the silane compound(s) of the formula (V) and the partial copolycondensation of the silane compound of the formula (V) and the above-mentioned other silane compound having etherified silanol groups can be conducted by the conventional known method of condensation of etherified silane compounds. Generally, these reactions are conducted by heating the reactants at room temperature to a temperature of up to the boiling point, preferably at 50° to 90° C., in the presence of water and an acid such as acetic acid or like organic acid or hydrochloric acid or like inorganic acid. The amount of water is variable suitably according to the degree of condensation desired.

The silane compound or resin having a polymerizable double bond and an etherified silanol group and the compound of the formula (III) or (IV) are subjected to an addition reaction, whereby a silane compound or resin is obtained which has a chelate forming group of the formula (I) or (II) and an etherified silanol group. The addition reaction can be conducted by reacting the two reactants usually at about 20° to about 100° C. for about 1 to about 24 hours, for example in the presence of an amine catalyst. The resin obtained by this method is included in the resins of the invention.

A resin of the invention can be obtained also by the partial condensation of the silane compound or resin obtained by the above addition reaction, or by subjecting the compound or resin, and other silane compound having etherified silanol groups to partial copolycondensation.

The above-mentioned other silane compound having etherified silanol groups can be any of those already mentioned for partial copolycondensation with the silane compound of the formula (V). The partial condensation and partial copolycondensation can be carried out by the same method as the partial (copoly)condensation already stated.

The resins of the invention obtained by these methods (4) have an etherified silanol group, which reacts with water in the air for hydrolysis, forming a silanol group to effect crosslinking. Thus, the resins can be of the moisture curing type.

The resin prepared by the method (1), (2) or (3), when having an etherified silanol group introduced thereinto, can also be made curable with moisture. The etherified silanol group can be introduced into the resin, for example, by causing the resin to contain a hydroxyl group, and reacting a monoisocyanate compound having an etherified silanol group with the hydroxyl group, for example, in the presence of a tin catalyst at about 20° to about 100° C. for about 1 to about 10 hours. Typical examples of monoisocyanate compounds having an etherified silanol group are γ-isocyanatopropyltrimethoxysilane, γ-isocyanatopropyltriethoxysilane and the like.

The resin of the invention may be one obtained by a method other than the methods (1) to (4) or modifications of these methods.

Preferably, the resin of the present invention has film forming ability. It is suitable that the resin be about 570 to 100000, more preferably about 800 to 50000, in number average molecular weight. It is required that the resin of the invention have at least one of the foregoing chelate forming group per molecule. Preferably the resin has 1 to 300, more preferably 2 to 200, chelate forming groups per molecule.

As already stated, various base resins are usable for preparing the resins of the invention. Examples of such resins are acrylic resins, epoxy resins, polyester resins, alkyl resins, silicon-containing resins, etc.

The resin of the invention may be used as diluted with an organic solvent, or as dispersed or dissolved in water after adjusting the amount of carboxyl groups in the resin so that the acid value thereof is 30 to 130 and neutralizing the carboxyl groups with an organic amine, ammonia or like base.

Further a reactive group such as hydroxyl can be incorporated into the resin of the invention in addition to the chelate forming group to use the resin in combination with a crosslinking agent reactive with the incorporated reactive group. In the case where the reactive group is, for example, hydroxyl, the resin can be crosslinked at room temperature or by heating using as the crosslinking agent a known one such as polyisocyanate compound, blocked polyisocyanate compound, amino resin, i.e., a condensation product of urea, melamine, benzoguanamine or like nitrogen-containing compound with formaldehyde, or a lower alkyletherified product of the condensate (with $C_1$ to $C_4$ alkyl).

The resin (a) for use in the photopolymerizable composition of the present invention comprises the corrosion preventive resin which has introduced thereinto at least one mole of polymerizable double bond per 1000 g of the resin.

The resin (a) can be prepared by utilizing the methods (1) to (4) for obtaining the corrosion preventive resins.

More specifically, the resin (a) can be obtained by the method (1) wherein a resin having a polymerizable double bond at a terminal position or side chain thereof and a compound represented by the formula (III) or (IV) are subjected to an addition reaction in such a quantitative ratio that at least one mole of polymerizable double bond remains per 1000 g of the resin obtained by the reaction.

When the method (2) is utilized, the specified amount of polymerizable double bonds are introduced into the molecules utilizing the reaction between the first functional group, such as hydroxyl, and the second functional group, such as isocyanate, simultaneously with or after the introduction of a chelate forming group of the formula (I) or (II).

Examples of combinations of first and second functional groups are hydroxyl-isocyanate, isocyanatehydroxyl, hydroxyl-acid anhydride, hydroxyl-acid chloride, etc.

The polymerizable double bond can be introduced into the molecule simultaneously with the introduction of the chelate forming group, for example, by reacting the addition reaction product (i) of a compound having both the first functional group and the polymerizable double bond and a compound represented by the formula (III) or (IV) with a compound or resin (ii) having the second functional group, with the addition to the reaction system of the compound having both the first functional group and the polymerizable double bond.

The polymerizable double bond can be introduced into the molecule after the introduction of the chelate forming group by reacting the addition reaction product (i) with the compound or resin (ii) having the second functional group, with an excessive amount of second functional groups present, and subsequently reacting the resulting product having the second functional group with the compound having both the first functional group and the polymerizable double bond.

It is required that the compound or resin (ii) having the second functional group have at least two second functional groups in the molecule. When the second functional group is isocyanate, examples of useful compounds or resins (ii) are hexamethylene diisocyanate, trimethylene diisocyanate, 1,4-tetramethylene diisocyanate, pentamethylene diisocyanate, 1,2-propylene diisocyanate, 1,2-butylene diisocyanate, trimethylhexamethylene diisocyanate, dimer acid diisocyanate, lysine diisocyanate and like aliphatic diisocyanates; isophorone diisocyanate, 4,4'-methylenebis(cyclohexylisocyanate), methylcyclohexane-2,4-(or -2,6-) diisocyanate, 1,3- (or 1,4-) di(isocyanatomethyl)cyclohexane and like alicyclic diisocyanates; xylylene diisocyanate, m-xylylene diisocyanate, tetramethylxylylene diisocyanate, tolylene diisocyanate, 4,4'-diphenylmethane diisocyanate, hydrogenated diphenylmethane diisocyanate, 4,4'-diphenyl diisocyanate, 1,5-naphthalene diisocyanate, 1,4-naphthalene diisocyanate and like aromatic diisocyanates; dianisidine diisocyanate, chlorodiphenylene diisocyanate, 4,4'-diphenyl ether diisocyanate and like heterocyclic diisocyanates; triphenylmethane-4,4',4"-triisocyanate, 1,3,5-triisocyanatobenzene, 2,4,6-triisocyanato toluene, 4,4'-dimethyldiphenylmethane-2,2',5,5'-tetraisocyanate and like polyisocyanates having at least three isocyanate groups in the molecule; adducts obtained by reacting a compound containing active hydrogen, such as ethylene glycol, propylene glycol, 1,4-butylene glycol, trimethylolpropane or pentaerythritol, with such a di- or poly-isocyanate in the presence of an excess of isocyanate relative to active hydrogen; biuret-type adducts of such di- or poly-isocyanates, isocyanurate ring type adducts; etc.

Examples of compounds or resins (ii) wherein the second functional group is hydroxyl are ethylene glycol, propylene glycol, diethylene glycol, triethylene glycol, tetraethylene glycol, butanediol, 3-methyl-1,2-butanediol, pentanediol, tetramethylene glycol, neopentyl glycol, 1,4-cyclohexanedimethanol, triscyclodecanedimethanol, hydrogenated bisphenol A, hydrogenated bisphenol F, hydroxypivalic acid-neopentyl glycol ester and like dihydric alcohols; trihydric to polyhydric alcohols such as glycerin, trimethylolpropane, trimethylolethane, diglycerin, triclycerin, 1,2,6-hexanetriol, pentaerythritol, dipentaerythritol, sorbitol and mannitol; polylactone polyols obtained by adding ε-caprolactone or like lactone to such alcohols; adduct of bisphenol A with alkylene oxide; vinyl copolymer polyol; polyester polyol; etc.

Examples of useful compound having both a polymerizable double bond and a first functional group which is hydroxyl are 2-hydroxyethyl acrylate, hydroxypropyl acrylate, hydroxybutyl acrylate, 2-hydroxyethyl methacrylate, hydroxypropyl methacrylate, hydroxybutyl methacrylate, adduct of acrylic acid or methacrylic acid with a polyol having an ε-caprolactone chain, allyl alcohol and the like. Examples of like compounds wherein the first functional group is isocyanate are isocyanatoethyl (meth)acrylate, m-isopropenylphenyl isocyanate, m-isopropenyl-α,α-dimethylbenzyl isocyanate, etc. Examples of like compounds wherein the first functional group is an acid anhydride are maleic anhydride, itaconic anhydride, etc. Examples of like compounds wherein the first functional group is an acid chloride are (meth)acrylic acid chloride, crotonic acid chloride, acid chloride of meleic acid half ester, acid chloride of fumaric acid half ester, etc.

When the method (3) is utilizied, the specified amount of polymerizable double bond can be introduced into the molecule by using a polymerizable unsaturated monomer having a first functional group such as hydroxyl as at least a portion of the aforementioned other polymerizable unsaturated monomer to be copolymerized, and thereafter reacting the resulting copolymer with a compound having a polymerizable double bond and a second functional group, such as isocyanate, which is reactive with the first functional group.

Further the polymerizable double bond can be introduced into the resin by the method (4) wherein a compound represented by the formula (III) or (IV) and a silane compound or resin having an etherified silanol group and polymerizable double bond subjected to an addition reaction in such a quantitative ratio that at least one mole of polymerizable double bond remains in the resulting resin per 1000 g thereof.

The resin (a) for use in the composition of the present invention preferably has film forming ability. It is suitable that the resin have a number average molecular weight of about 570 to about 100000, more preferably about 800 to about 50000. It is required that the resin have at least one of the chelate forming groups described above per molecule. Preferably, the resin has 1 to 300, more preferably 2 to 200, chelate forming groups per molecule. It is further required that the resin (a) have at least one mole of polymerizable double bond in the molecule per 1000 g of the resin. Preferably, the resin has 1.5 to 4.0 moles, more preferably 1.5 to 3.0 moles, of polymerizable double bond per 1000 g thereof.

Various ba·e resins are usable for preparing the resin (a). Examples of such resins are acrylic resins, epoxy resins, polyester resins, silicon-containing resins, etc.

The resin (a) may be used as diluted with an organic solvent, polymerizable unsaturated monomer, polyvinyl monomer containing at least two polymerizable double bonds in the molecule, or a mixture of such monomers. Alternatively, the resin may be used as dispersed or dissolved in water after adjusting the amount of carboxyl groups in the resin so that the acid value thereof is 30 to 130 and neutralizing the carboxyl groups with an organic amine, ammonia or like base.

Examples of photopolymerization initiators for use with the resin (a) for preparing the composition of the present invention are benzoin, benzoin methyl ether, benzoin ethyl ether, benzyl, benzyl dimethyl ketal, diphenyl disulfide, tetramethylthiuram monosulfide, diacetyl, Eosine, Thionine, Michler's ketone, anthracene, anthraquinone, chloroanthraquinone, methylanthraquinone, α-hydroxyisobutylphenone, p-isopropyl-α-hydroxyisobutylphenone, acetophenone, α,α-dichloro-4-phenoxyacetophenone, 1-hydroxy-1-cyclohexylacetophenone, 2,2-dimethoxy-2-phenylacetophenone, methylbenzoyl formate, 2-methyl-1-[4-(methylthio)-phenyl].2.morpholinopropene, thioxanthone, benzophenone, etc. These photopolymerization initiators are usable in combination with a sensitizer.

The photopolymerization initiator is used in the composition of the present invention preferably in an amount of 0.1 to 20 parts by weight, more preferably 0.5 to 10 parts by weight, per 100 parts by weight of the resin (a). In the case where the initiator is used in combination with the sensitizer, it is desirable that the combined amount of the two agents be within the above range. The ratio of the initiator to the sensitizer is 1.0:1.0 to 1.0:0.01 by weight.

The photopolymerizable composition of the invention may consist only of the resin (a) and the photopolymerization initiator (b). In view of ease of application, etc., however, the composition is used as dissolved in an organic solvent, or in the form of a monomer solution as described above, or in the form of an aqueous solution or aqueous dispersion when a water-miscible solvent is used as the solvent for preparing the resin. In this case, water is added to the resulting resin liquid or the liquid is admixed with water.

The solvent to be used is not limited specifically insofar as it is capable of dissolving or dispersing the component (a) and the component (b) of the invention. Examples of useful solvents are ethyl acetate, butyl acetate and like acetic acid esters; ethylene glycol, diethylene glycol, propylene glycol and like glycol ethers; toluene, xylene and like aromatic hydrocarbons; methanol, ethanol, butanol and like alcohols; methyl ethyl ketone, methyl isobutyl ketone and like ketones, water; etc. These solvents can be used singly or in admixture in an amount as suitably adjusted, for example, according to the method of application of the composition.

The unsaturated monomer to be used is not limited specifically insofar as it is capable of dissolving or dispersing the components (a) and (b). Examples of useful monomers are the unsaturated monomers given as examples of "other polymerizable unsaturated monomers" for the method (3), mono- or di-(meth)acrylic acid esters of ethylene glycol, propylene glycol and like glycols, polyetherified products of such glycols; di-, tri- or tetra-(meth)acrylic acid esters of trimethylolpropane and pentaerythritol and like polyvinyl monomers. The monomer is used preferably in an amount of up to 30 parts by weight per 100 parts by weight of the resin (a), and may be used in combination with the solvent mentioned.

When required, the photopolymerizable composition of the present invention may have further incorporated therein coloring pigment, extender pigment, corrosion inhibitive pigment, dye, thermoplastic polymer, crosslinking agent, leveling agent, defoaming agent, antisagging agent and like additives. The coloring pigment, extender pigment, corrosion inhibitive pigment and dye to be used are those usually used in the field of inks and paints. These additives are used in an amount of up to 75 wt.%, preferably up to 50 wt.%, based on the solids content of the present composition. When the resin (a) contains hydroxyl as a functional group, the crosslinking agent mentioned is used for the agent and the hydroxyl group to cause crosslinking at room temperature or with heating, in addition to photopolymerization due to the polymerizable double bond. Examples of useful crosslinking agents are those already known such as a polyisocyanate compound, blocked polyisocyanate compound, amino resin, i.e., a condensation product of urea, melamine, benzoquanamine or like nitrogen-containing compound with formaldehyde, and lower alkyletherified product of such a condensate (the alkyl having 1 to 4 carbon atoms).

Further the resin (a), when prepared by the method (4), contains etherified silanol groups which can be subjected to hydrolysis or condensation, so that the resin can be crosslinked by hydrolysis due to moisture or water and condensation of the silanol groups, besides photopolymerization due to the polymerizable double bond.

The photopolymerizable composition of the invention thus obtained is applied to substrates by spray coating, brush coating, roller coating, dip coating, electrophoretic coating, silk-screen printing or like usual method generally to a thickness of 0.1 to 50 μm when dried. The uncured coating formed is cured by being irradiated with active rays, such as ultraviolet rays, at a dose of 0.1 mj/cm$^2$ to 500 mj/cm$^2$, preferably 1 mj/cm$^2$, to 200 mj/cm$^2$.

The irradiator to be used is one conventionally used for curing with ultraviolet rays or like active rays, such as superhigh-pressure mercury lamp, high-pressure mercury lamp or visible-ray laser.

When the substrate has the surface of a metal such as iron, zinc, tin, copper, aluminum or the like or of an alloy of such metals, and when the substrate has such a surface which is subjected to a chemical conversion treatment as with chromic acid or a phosphate, the substrate can be given high corrosion resistance by forming a cured coating of the present composition on the surface.

In the case where the coating cured with light contains a crosslinking agent which undergoes a crosslinking reaction with the functional group, such as hydroxyl, in the resin, heating of the coating, for example, at about 80° to about 180° C. for 10 to 60 minutes, gives an increased crosslinking density and improved strength to the coating.

The coating formed by the present composition can be thus heated after another coating has been formed thereon.

The corrosion preventive resin of the present invention, as used singly or in combination with a crosslinking agent, gives high corrosion resistance to metals, such as iron, zinc, copper and aluminum, which release positive bivalent or trivelent metal ions on corrosion, without entailing any pollution. Further the photopolymerizable composition of the invention imparts high corrosion resistance to such metals when applied thereto, and forms coatings rapidly free of pollution.

Accordingly, the resin and the composition of the present invention are very useful as surface treating agents and corrosion preventive coating compositions for metals.

The present invention will be described in greater detail with reference to the following examples, in which the parts and percentages are all by weight unless otherwise specified.

Preparation and Properties of Corrosion Preventive Resin of the Invention

Preparation Example 1

Methyl Isobutyl ketone (245.3 parts) was placed into a flask and heated to 50° C., and nitrogen gas was introduced into the flask to replace the air by the gas. The following mixture was further placed into the flask.

| 2-Hydroxyethyl acrylate | 116 parts |
| Thioglycollic acid | 92 parts |
| Triethylamine | 1.8 parts |

The resulting mixture was heated at 50° C. for 5 hours and reacted at 80° C. for 1 hour with heating to obtain a solution of hydroxyl-containing adduct. The solution obtained was checked by a color reaction using 5,5'- dithiobis(2-nitrobenzoic acid) to ascertain that no SH group remained due to the addition of SH groups of the thioglycollic acid to the 2-hydroxyethyl acrylate.

Next, air was placed into the flask in place of nitrogen, and the following mixture was added to the adduct solution.

| m-Isopropenylphenyl isocyanate | 116 parts |
|---|---|
| Dibutyltin diacetate | 0.2 part |
| Hydroquinone | 0.4 part |

While introducing air into the flask, the resulting mixture was heated at 50° C. for 5 hours and then at 80° C. for 1 hour to obtain a monomer A solution. The resin solution obtained had a solids content of about 60%. The main structure of monomer A is represented by the following formula.

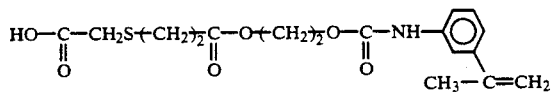

Preparation Example 2

Water (1000 parts) was placed into a flask, nitrogen gas was introduced into the flask to replace the air, and the following compounds were placed in.

| γ-Methacryloyloxypropyl-trimethoxysilane | 248 parts |
|---|---|
| Thiosalicylic acid | 154 parts |
| Triethylamine | 3.0 parts |
| Methoxypropanol | 402 parts |

The compounds were mixed together with stirring and then heated at 50° C. for 5 hours and thereafter at 80° C. for 1 hour in the nitrogen gas atmosphere to obtain a silane B solution having about 50% solids content. The main structure of silane B is represented by the following formula

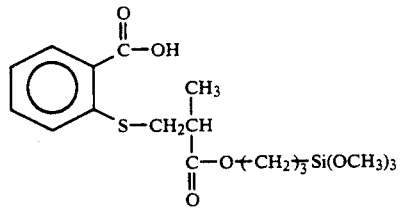

Preparation Example 3

Water (2000 parts) was placed into a flask, nitrogen gas was introduced into the flask to replace the air, and the following compounds were placed in.

| Thiosalicylic acid | 308 parts |
|---|---|
| Allyl bromide | 242 parts |
| Nickel chloride | 238 parts |
| Sodium carbonate | 106 parts |

The above compounds were mixed together with stirring and then allowed to stand at room temperature (20° C.) for 24 hours in the nitrogen gas atmosphere to obtain a precipitate. The precipitate was filtered off, washed with water and then placed into another flask containing 1000 parts of 5N aqueous solution of acetic acid solution, followed by stirring and thereafter by filtration. The resulting cake was dried to obtain allylthiosalicylic acid.

The allylthiosalicylic acid (194 parts) was dissolved in 427 parts of methyl isobutyl ketone. To the solution was added 78 parts of mercaptoethanol, and the mixture was heated at 80° C. for 8 hours with stirring and with introduction of nitrogen gas to obtain a hydroxyethylthiopropylthiosalicylic acid solution containing about 39% of solids. To the solution (699 parts) thereafter cooled to 50° C. were added the following compounds, and the mixture was heated at 50° C. for 7 hours in a nitrogen gas atmosphere to obtain a monomer C solution.

| Isocyanatoethyl methacrylate | 155 parts |
|---|---|
| Dibutyltin diacetate | 0.21 part |
| Hydroquinone | 0.43 part |

The solution obtained had a solids content of about 50%. The main structure of monomer C is represented by the following formula.

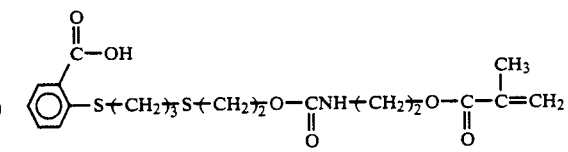

Preparation Example 4

Methyl isobutyl ketone (47 parts) was placed into a flask and heated at 50° C. With introduction of nitrogen into the flask, the following compounds were added to the ketone.

| Hydroxyethylthiopropylthiosalicylic acid solution having solid content of about 39% and used in Prep. Ex. 3 | 699 parts |
|---|---|
| γ-Isocyanatopropyltrimethoxysilane | 205 parts |
| Dibutyltin diacetate | 0.24 part |

The compounds were thereafter heated at 50° C. for 7 hours and then at 80° C. for 1 hour in the nitrogen stream. The reaction mixture was thereafter cooled and diluted with 636 parts of ethanol to obtain a silane D solution, which contained about 30% of solids.

The main structure of silane D is represented by the following formula.

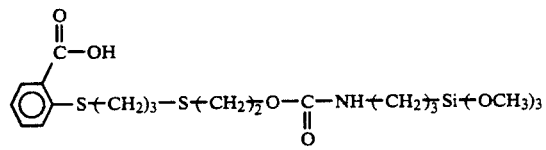

Preparation Example 5

Into a flask were placed 1000 parts of water, 194 parts of allylthiosalicylic acid and 101 parts of triethylamine to prepare a uniform solution. To the solution were added 62 parts of 2,3-dimercapto-1-propanol and 0.5 part of chloroplatinic acid. The mixture was heated at 80° C. for 8 hours with stirring and with introduction of nitrogen gas to give 1-hydroxypropane-2,3-di(thio-S-γ-propylthiosalicylic acid) represented by the following formula.

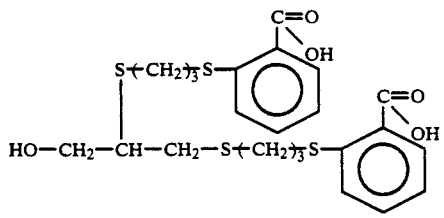

Methyl isobutyl ketone (446 parts were placed into another flask and heated at 5° C. The following compounds were added to the ketone while introducing air into the flask.

| 1-Hydroxypropane-2,3-di(thio-S-γ-propylthiosalicylic acid | 514 parts |
| --- | --- |
| Isocyanatoethyl methacrylate | 155 parts |
| Dibutyltin diacetate | 0.33 part |
| Hydroquinone | 0.66 part |

The mixture was thereafter heated at 50° C. for 7 hours in the air stream to obtain a monomer E solution. The main structure of monomer E is represented by the following formula.

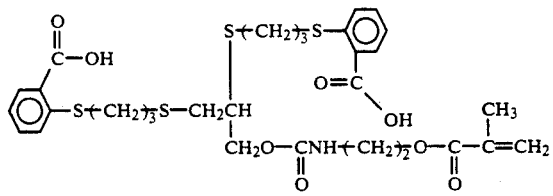

Preparation Example 6

Methyl isobutyl ketone (719 parts) was placed into a flask and heated at 50° C. The following compounds were added to the ketone while introducing nitrogen gas into the flask.

| 1-Hydroxypropane-2,3-di(thio-S-γ-propylthiosalicylic acid | 514 parts |
| --- | --- |
| γ-Isocyanatopropyl trimethoxysilane | 205 parts |
| Dibutyltin diacetate | 0.36 part |

The mixture was thereafter heated at 50° C. for 7 hours and subsequently at 80° C. for 1 hour in the nitrogen gas stream. To the reaction mixture then cooled was added 959 parts of ethyl alcohol to obtain a silane F solution, which contained 30% solids. The main structure of silane F is represented by the following formula.

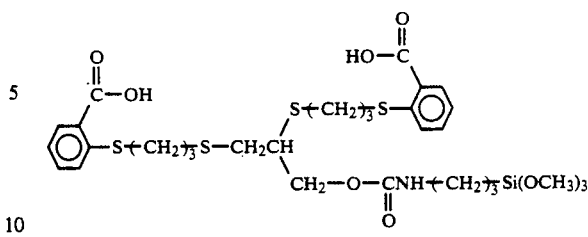

EXAMPLE 1

Isobutyl alcohol (20 parts) and 38.7 parts of methyl isobutyl ketone were placed into a flask and held heated at 90° C. while introducing nitrogen gas into the flask. A uniform solution of mixture of the following monomers and polymerization initiator was added dropwise to the mixture over a period of 4 hours.

| Monomer A solution having solid content of about 60% and obtained in Prep. Ex. 1 | 20 parts |
| --- | --- |
| 2-Hydroxyethyl methacrylate | 20 parts |
| Styrene | 30 parts |
| n-Butyl acrylate | 38 parts |
| 2,2'-Azobisisobutyronitrile | 1.5 parts |

One-half quantity of mixture of 30.8 parts of toluene and 1.0 part of 2,2'-azobis-2,4-dimethylvaleronitrile was thereafter added dropwise to the resulting mixture over a period of 1 hour at the same temperature. The other half of the mixture was then added dropwise to the mixture at an elevated temperature of 100° C. over a period of 1 hour. The resulting mixture was thereafter maintained at the same temperature for 1 hour and subsequently cooled. To the mixture was added 50 parts of isopropyl alcohol to obtain a resin solution, which contained about 40% of solids. The resin had a number average molecular weight of about 26000 and 8.5 chelate forming groups per molecule on the average. The following ingredients were admixed with this resin solution to obtain composition A.

| Resin solution having about 40% solids content obtained above | 80 parts |
| --- | --- |
| CYMEL 303*[1] | 8 parts |
| Triethylamine | 6.8 parts |
| Isopropanol | 10.2 parts |
| Deionized water | 95 parts |
| The composition A obtained had a solids content of about 20%. | |

Note *[1]CYMEL 303: ethyletherified melamine resin having solids content of about 98% and manufactured by Mitsui Cyanamide Co., Ltd.

EXAMPLE 2

Isobutyl acetate (20 parts) and 31.7 parts of methyl isobutyl ketone were placed into a flask and held heated at 90° C. while introducing nitrogen gas into the flask. A uniform solution of the following monomers and polymerization initiator mixed together was added dropwise to the mixture over a period of 4 hours.

| Monomer C solution having solids content of about 50% and obtained in Prep. Ex. 3 | 30 parts |
| --- | --- |
| Acrylonitrile | 20 parts |
| n-Butyl acrylate | 35 parts |

-continued

| | |
|---|---|
| 2-Hydroxyethyl methacrylate | 30 parts |
| 2,2'-Azobisisobutyronitrile | 1.0 part |

One-half quantity of mixture of 16.2 parts of isobutyl acetate, 16.2 parts of methyl isobutyl ketone and 1.0 part of 2,2'-azobis-2,4-dimethylvaleronitrile was thereafter added dropwise to the mixture at the same temperature over a period of 1 hour. The other half of the mixture was then added dropwise to the resulting mixture at an elevated temperature of 100° C. over a period of 1 hour. The mixture obtained was subsequently maintained at the same temperature for 1 hour and thereafter cooled. Next, 53.0 parts of γ-isocyanatopropyltrimethoxysilane and 0.08 part of dibutyltin diacetate were added to the mixture, followed by reaction at 50° C. for 9 hours and then by cooling. Ethanol (410.9 parts) and 100 parts of toluene were added to the cooled mixture to prepare a resin C solution, which had a solids content of about 20%. Resin C had a number average molecular weight of about 30000 and 6.9 chelate forming groups per molecule on the average.

EXAMPLE 3

Methyl isobutyl ketone (59 parts) was placed into a flask and held heated at 90° C. while introducing nitrogen gas into the flask. A uniform solution of the following monomers and polymerization initiator mixed together was added dropwise to the ketone over a period of 4 hours.

| | |
|---|---|
| Monomer E solution having solids content of about 60% and obtained in Prep. Ex. 5 | 16.7 parts |
| 2-Hydroxyethyl acrylate | 22 parts |
| Isobutyl methacrylate | 58 parts |
| Acrylic acid | 10 parts |
| 2,2'-Azobisisobutyronitrile | 1.0 parts |

One-half quantity of mixture of 31.4 parts of toluene and 2 parts of 2,2'-azobis-2,4-dimethylvaleronitrile was thereafter added dropwise to the mixture at the same temperature over a period of 1 hour. The other half of the mixture was then added dropwise to the resulting mixture at an elevated temperature of 100° C. over a period of 1 hour. The mixture obtained was thereafter maintained at the same temperature for 1 hour, followed by cooling and by addition of 70 parts of isobutyl acetate and 63.2 parts of methyl isobutyl ketone to the cooled mixture to prepare a resin solution. The solution obtained had a solids content of about 30%. The resin was about 20000 in number average molecular weight and had 6.0 chelate forming groups per molecule on the average.

The following ingredients were admixed with this resin solution to obtain composition E.

| | |
|---|---|
| Resin solution having solids content of about 30% obtained above | 80 parts |
| Isophorone diisocyanate | 6 parts |
| Isobutylketone | 14 parts |

The resulting composition E had a solids content of about 30%.

EXAMPLE 4

The following mixture was placed into a flask.

| | |
|---|---|
| Silane B solution having solids content of about 50% and obtained in Prep. Ex. 2 | 482 parts |
| Vinyltrimethoxysilane | 296 parts |
| Phenyltrimethoxysilane | 198 parts |
| Ethanol | 115 parts |
| Deionized water | 194 parts |
| Toluene | 1038 parts |

The mixture was heated at 80° C. for 8 hours for reaction, and the reaction mixture was distilled to remove 1300 parts of solvent therefrom. The reaction product in the flask was then cooled, and 1410 parts of ethanol was added thereto to obtain a resin B solution, which had a solids content of about 20%. The resin was about 15000 in number average molecular weight and had 26 chelate forming groups per molecule on the average.

EXAMPLE 5

The following mixture was placed into a flask.

| | |
|---|---|
| Monomer D solution having solids content of about 30% and obtained in Prep. Ex. 4 | 477 parts |
| Vinyltrimethoxysilane | 148 parts |
| Methyltrimethoxysilane | 136 parts |
| Toluene | 538.5 parts |
| Deionized water | 124.2 parts |

The mixture was stirred, heated at 80° C. for 8 hours and then distilled to remove 795.9 parts of solvent. The product in the flask was thereafter cooled, and 2511.2 parts of ethanol was added thereto to obtain a resin D solution, which had a solids content of about 20%. The resin was about 20000 in number average molecular weight and had 54 chelate forming groups per molecule on the average.

EXAMPLE 6

The following mixture was placed into a flask.

| | |
|---|---|
| Monomer F solution having solids content of about 30% and obtained in Prep. Ex. 6 | 719 parts |
| Vinyltrimethoxysilane | 215.1 parts |
| Ethanol | 250.3 parts |
| Deionized water | 95 parts |

The mixture was stirred, heated at 80° C. for 8 hours, and then distilled to remove 340 parts of solvent. The reaction product in the flask was thereafter cooled, and 4902 parts of ethanol was added thereto to obtain a resin F solution, which had a solids content of about 5%. The resin had a number average molecular weight of about 10000 and 49 chelate forming groups per molecule on the average.

EXAMPLE 7

The following mixture was placed into a flask and reacted at 115° C. for 10 hours while introducing air into the flask.

| | |
|---|---|
| EPIKOTE 1001*2 | 1000 parts |
| Acrylic acid | 72 parts |
| Tetraethylammonium bromide | 5.4 parts |
| Hydroquinone | 1.1 parts |

-continued

| Methoxypropanol | 1065.5 parts |

Note *²EPIKOE 1001: brand name of bisphenol A type epoxy resin (about 900 in molecular weight), product of Shell Chemical Co, Ltd The reaction mixture was cooled at 100° C., 106 parts of 2-mercaptopropionic acid and 70 parts of triethylamine were added to the mixture, and the resulting mixture was reacted at 100° C. for 8 hours. The reaction mixture obtained was cooled to obtain a resin solution, which had a solids content of about 50%. The resin was about 970 in number average molecular weight and had 1.0 chelate forming group per molecule on the average.

The following ingredients were admixed with the resin solution prepared to obtain composition G.

| Resin solution having solids content of about 50% obtained above | 80 parts |
| CYMEL 303 | 10 parts |
| Deionized water | 410 parts |

The resulting composition G had a solids content of about 10%.

Test Examples 1-7

Each of the resin solutions or compositions A to G obtained in Examples 1 to 7 was applied to various substrates to a thickness of 0.5 μm when dried and dried under the conditions listed in Table 1. The coating was further coated with an epoxy-melamine coating composition (KP COLOR 8451 primer, manufactured by Kansai Paint Co., Ltd.) to a thickness of about 5 μm when dried, and the coating was baked at 140° C. for 20 minutes for curing. The coated panels thus obtained were subjected to a salt spray test, filiform corrosion test and outdoor exposure test. Table 1 shows the test results.

For comparative tests, panels treated with chromic acid or zinc phosphate by the conventional method and untreated panels were similarly coated with the above epoxy-melamine coating composition, baked for curing and tested. Table 1 also shows the results obtained.

Test Methods

Salt spray test (SST)

Cut flaws of approximately 40 mm in length intersecting mutually at the angle of 30 degree, reaching the substrate by using a cutter knife on the middle part of the coated panel and tested according to JIS Z 2371. The duration of salt spraying was 500 hours.

Filiform corrosion test (FCT)

Cut flaws were formed similarly as the salt spray test on the coated panel, and then the panel was held with the coating surface down on the upper portion of a beaker containing 1N hydrochloric acid to expose the cross-cutted coating surface to the vapor of hydrochloric acid, the beaker was then sealed off, and the coating was thus exposed to the acid vapor for 1 hour. The panel was thereafter subjected to a wetting test under the condition of 50±2° C. and RH of 98±2% for 1000 hours.

Outdoor exposure test (EPT)

Cut flaws were formed similarly as the salt spray test on the coated panel, and the coating was held directed toward the south at 30 degree according to JIS K 5400 9.9 (1990) for 6 months.

The coated panels thus tested were checked for the width of peeling of the coating and maximum length of corrosion on one side of the cut lines. Table 1 shows the results.

Table 1 reveals that the resins of the invention and the compositions each comprising the resin of the invention, crosslinking agent, etc. give higher corrosion resistance than the conventional surface-treating compositions to various substrates.

TABLE 1

| | Test Example | | | | | | |
|---|---|---|---|---|---|---|---|
| Example No. | 1 | 2 | 3 | 4 | 5 | 6 | 7 |
| Resin or composition | A | C | E | B | D | F | G |
| Drying condition | 140° C., 20 min | r.t., 3 days | 80° C., 20 min | r.t., 3 days | r.t., 3 days | r.t., 3 days | 140° C., 20 min |
| Substrate, test item | | | | | | | |
| Zn-plated steel panel | | | | | | | |
| SST (mm) | 1.5 | 1.2 | 1.0 | 0.8 | 1.2 | 0.3 | 0.8 |
| FCT (mm) | 0.5 | 0.3 | 0.6 | 0.7 | 0.6 | 0.1 | 0.5 |
| EPT (mm) | 0.3 | 0.2 | 0.1 | 0.3 | 0.3 | 0.2 | 0.2 |
| Cold-rolled steel panel | | | | | | | |
| SST (mm) | 2.5 | 2.0 | 2.5 | 2.0 | 0.3 | 0.4 | 0.8 |
| FCT (mm) | 1.0 | 0.8 | 1.5 | 1.2 | 0.2 | 0.6 | 0.8 |
| EPT (mm) | 0.6 | 0.6 | 0.9 | 1.1 | 0.1 | 0.3 | 0.2 |
| Sn-plated steel panel | | | | | | | |
| SST (mm) | 0.3 | 0.9 | 0.3 | 0.3 | 0.2 | 0.1 | 0.2 |
| FCT (mm) | 0.2 | 0.5 | 0.1 | 0.2 | 0.1 | 0.0 | 0.2 |
| EPT (mm) | 0.5 | 0.2 | 0.1 | 0.0 | 0.1 | 0.0 | 0.2 |
| Cr-plated steel panel | | | | | | | |
| SST (mm) | 0.7 | 0.6 | 0.2 | 0.2 | 0.1 | 0.0 | 0.2 |
| FCT (mm) | 0.1 | 0.1 | 0.2 | 0.1 | 0.0 | 0.0 | 0.1 |
| EPT (mm) | 0.0 | 0.0 | 0.1 | 0.2 | 0.0 | 0.0 | 0.2 |
| SUS 304 | | | | | | | |
| SST (mm) | 0.2 | 0.0 | 0.0 | 0.0 | 0.0 | 0.0 | 0.0 |
| FCT (mm) | 0.0 | 0.0 | 0.0 | 0.0 | 0.0 | 0.0 | 0.0 |
| EPT (mm) | 0.0 | 0.0 | 0.0 | 0.0 | 0.0 | 0.0 | 0.0 |
| Al panel | | | | | | | |
| SST (mm) | 0.2 | 0.3 | 0.3 | 0.3 | 0.3 | 0.0 | 0.0 |
| FCT (mm) | 0.3 | 0.4 | 0.7 | 0.6 | 0.6 | 0.2 | 0.1 |
| EPT (mm) | 0.0 | 0.1 | 1.0 | 0.8 | 0.5 | 0.1 | 0.0 |

| | Comparative Test Example | | |
|---|---|---|---|
| Example No. | 1 | 2 | 3 |

TABLE 1-continued

| Treatment | | Chromic acid | Zinc phosphate | None |
| --- | --- | --- | --- | --- |
| Substrate, test item | | | | |
| Zn-plated steel panel | SST (mm) | 4.0 | 10< | 20< |
| | FCT (mm) | 5.0 | 7.5 | 10< |
| | EPT (mm) | 2.7 | 3.5 | 5.0 |
| Cold-rolled steel panel | SST (mm) | 3.0 | 8 | 20< |
| | FCT (mm) | 2.7 | 5 | 10 |
| | EPT (mm) | 1.9 | 3 | 7.0 |
| Sn-plated steel panel | SST (mm) | 2.0 | | 2.5 |
| | FCT (mm) | 2.5 | | 3.5 |
| | EPT (mm) | 1.0 | | 2.0 |
| Cr-plated steel panel | SST (mm) | | | 1.5 |
| | FCT (mm) | | | 1.0 |
| | EPT (mm) | | | 2.3 |
| SUS 304 | SST (mm) | | | 0.8 |
| | FCT (mm) | | | 0.5 |
| | EPT (mm) | | | 0.4 |
| Al panel | SST (mm) | 0.5 | | 0.8 |
| | FCT (mm) | 0.9 | | 3.7 |
| | EPT (mm) | 1.5 | | 2.0 |

Note
"r.t." means room temperature.

Preparation and Properties of Photopolymerizable Composition

Preparation Example 7

1-Methoxy-2-propanol (300 parts) was placed into a flask and heated to 100° C. The following mixture was added dropwise to the propanol over a period of 3 hours.

| Methyl methacrylate | 150 parts |
| --- | --- |
| Acrylic acid | 250 parts |
| Styrene | 50 parts |
| 2-Hydroxyethyl methacrylate | 50 parts |
| 2,2'-Azobisisobutyronitrile | 30 parts |

The reaction mixture was maintained at the same temperature for 4 hours to obtain an acrylic resin solution.

The following mixture was then added to the solution.

| Glycidyl methacrylate | 426 parts |
| --- | --- |
| Hydroquinone | 0.08 part |
| Tetraethylammonium bromide | 0.8 part |

The resulting mixture was heated at 100° C. for 10 hours to obtain a solution of carboxyl-containing unsaturated acrylic resin.

A mixture of 154 parts of thicsalicylic acid and 580 parts of 1-methoxy-2-propanol was then added to the resin solution, followed by a reaction at 70° C. for 12 hours to prepare a chelate resin H solution.

The solution obtained was checked by a color reaction using 5,5'-dithiobis(2-nitrobenzoic acid) to ascertain that no SH group remained due to the addition of SH groups of the thiosalicylic acid to the carboxyl-containing unsaturated acrylic resin.

The solution obtained has a solids content of about 50%. The solid resin portion prepared was about 13000 in average number molecular weight and had 1.85 moles/kg of polymerizable double bond, 12.1 chelate forming groups per molecule on the average and an acid value of 76.

Preparation Example 8

Methyl isobutyl ketone (245 parts) was placed into a flask and heated at 50° C. With the inside air of the flask replaced by nitrogen gas, the following mixture was added to the ketone.

| 2-Hydroxyethyl acrylate | 116 parts |
| --- | --- |
| Thioglycollic acid | 92 parts |
| Triethylamine | 1.8 parts |

The resulting mixture was stirred and then heated at 50° C. for 5 hours and thereafter at 80° C. for 1 hour to obtain a hydroxyl-containing adduct solution (a).

Subsequently, with air introduced into the flask instead of nitrogen, the following mixture was admixed with the adduct solution.

| m-Isopropenyl-α,α-dimethylbenzyl isocyanate | 210 parts |
| --- | --- |
| Dibutyltin diacetate | 0.2 part |
| Hydroquinone | 0.02 part |

The resulting mixture was stirred and then heated at 70° C. for 5 hours and thereafter at 80° C. for 3 hours to obtain a solution of compound having a polymerizable unsaturated group. The compound solution had a solids content of about 60%. The main structure of the compound is represented by the following formula.

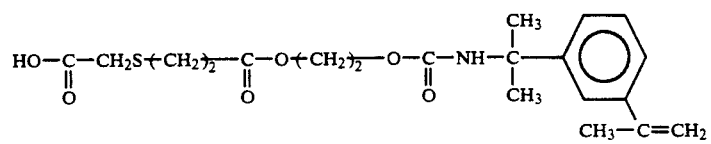

Methyl isobutyl ketone (58.7 parts) was placed into another flask and held heated at 90° C. while introducing nitrogen gas into the flask. A uniform solution of mixture of the following monomers and polymerization initiator was added dropwise to the ketone over a period of 4 hours.

| | |
|---|---|
| Compound solution having solids content of about 60% and obtained above | 40 parts |
| Hydroxyethyl acrylate | 30 parts |
| Styrene | 20 parts |
| n-Butyl acrylate | 25.4 parts |
| 2,2'-Azobisisobutyronitrile | 1.5 parts |

One-half quantity of mixture of 30.8 parts of toluene and 1.0 part of 2,2'-azobis-2,4-dimethylvaleronitrile was thereafter added dropwise to the resulting mixture at the same temperature over a period of 1 hour. The remaining half of the mixture was subsequently added dropwise to the mixture obtained at an elevated temperature of 100° C. over a period of 1 hour. The mixture was subsequently maintained at the same temperature for 1 hour and cooled. Dimethoxyethane (50 parts) was added to the cooled mixture to obtain a resin solution.

Isocyanatoethyl methacrylate (38 parts), 0.05 part of dibutyltin acetate and 0.001 part of hydroquinone were added to the resin solution, and the mixture was heated at 50° C. for 8 hours in an air stream to obtain a chelate resin I solution, which had a solids content of about 54%. The resin obtained had a number average molecular weight of about 34000, 1.77 moles/kg of polymerizable double bond, 15.0 chelate forming groups per molecule on the average and an acid value of 25.

Preparation Example 9

In 500 parts of 2-butoxyethanol was dissolved 500 parts of EPIKOTE 180S70 (cresol novolak type epoxy resin manufactured by Yuka Shell Epoxy Co., Ltd. and having a molecular weight of about 1000 and epoxy equivalent of about 200). While maintaining the solution at 100° C., the following compounds were added to the solution, followed by reaction for 10 hours to obtain an unsaturated resin solution.

| | |
|---|---|
| Acrylic acid | 180 parts |
| Tetrabutylammonium chloride | 0.7 part |
| Monomethoxyhydroquinone | 0.01 part |

To the solution was added 115.5 parts of thiosalicylic acid, and the mixture was reacted at 100° C. for 4 hours to obtain a chelate resin J solution, which had solids content of about 61.5%. The resin obtained has a number average molecular weight of about 1600, 2.2 moles/kg of polymerizable double bond, 1.5 chelate forming groups per molecule on the average and an acid value of 53.

Preparation Example 10

A hydroxyl-containing adduct solution (b) was prepared in the same manner as in Preparation Example 2 with the exception of using 154 parts of thiosalicylic acid in place of 92 parts of thioglycollic acid used for preparing the adduct solution (a) in Preparation Example 8.

Into another flask was placed 500 parts of a solution containing 50% of solids and prepared by dissolving a polyisocyanate in dimethoxyethane, the polyisocyanate being an adduct comprising 1 mole of trimethylolpropane and 3 moles of tolylene diisocyanate. The adduct solution (b) (200 parts) and 0.3 part of dibutyltin laurate were added to the solution, followed by heating at 50° C. for 6 hours. With addition of 0.005 part of hydroquinone, 88.5 parts of hydroxyethyl acrylate and 100 parts of dimethoxyethane, the resulting mixture was further heated for 6 hours to obtain a chelate resin K solution, which had a solids content of about 49%. The resin obtained had a number average molecular weight of about 1150, 1.74 moles/kg of polymerizable double bond, 1.0 chelate forming group per molecule on the average and an acid value of 50.

Preparation Example 11

Into a flask was placed 402 parts of 1-methoxy-2-propanol, nitrogen gas was introduced into the flask to replaced the inside air, and the following compounds were placed in

| | |
|---|---|
| γ-Methacryloyloxypropyltrimethoxysilane | 248 parts |
| Thiosalicylic acid | 154 parts |
| Triethylamine | 3.0 parts |
| Methoxypropanol | 402 parts |

The mixture was stirred, and heated at 50° C. for 5 hours and then at 80° C. for 1 hour in the nitrogen gas atmosphere for reaction to obtain a silane (c) solution containing about 50% of solids. The main structure of silane (c) is represented by the following formula.

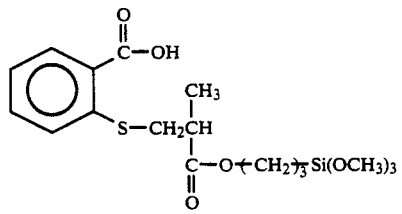

The following ingredients were then placed into another flask.

| | |
|---|---|
| Silane (c) solution having solids content of about 50% | 402 parts |
| γ-Methacryloyloxypropyltrimethoxysilane | 372 parts |
| Phenyltrimethoxysilane | 148.5 parts |
| Isobutyltrimethoxysilane | 133.5 parts |
| Deionized water | 100 parts |
| Toluene | 1000 parts |
| Concentrated hydrochloric acid | 2 parts |
| Hydroquinone | 0.1 parts |

The mixture was reacted at 80° C. for 3 hours and then heated for the removal of solvent while gradually raising the temperature. Upon the amount of solvent removed reaching 1000 parts, the heating was discontinued, followed by cooling. Ethanol (200 parts) was added to the product to obtain a chelate resin L solution, which had a solids content of about 38%. The resin obtained had a number average molecular weight of about 7000, 2.90 moles/kg of polymerizable double bond, 6.7 chelate forming groups per molecule on the average and an acid value of 54.

Examples 8–15

Photopolymerizable compositions of Examples 8 to 15 were prepared from the ingredients listed in Table 2 using chelate resin H to L-solutions obtained in Examples 7 to 11.

TABLE 2

| Ex. | Chelate resin solution Kind | Amount (parts) | Photopolymerization initiator Kind | Amount (parts) | Crosslinking agent Kind | Amount (parts) | Solvent Kind | Amount (parts) |
|---|---|---|---|---|---|---|---|---|
| 8 | H | 100 | α-Hydroxyiso-butylphenone | 2.5 | — | — | Methyl iso-butyl ketone | 100 |
| 9 | H | 100 | α-Hydroxyiso-butylphenone Benzophenone | 1.5 1.0 | Triglycidyl isocyanurate | 10 | Methyl iso-butyl ketone | 140 |
| 10 | I | 100 | Benzophenone | 2 | — | — | Methyl iso-butyl ketone | 100 |
| 11 | J | 100 | 2-Methyl-1-[4-methylthiophenyl]-2-morpholino-propene | 1.5 | — | — | 1-Methoxy-propanol | 150 |
| 12 | J | 100 | 2-Methyl-1-[4-methylthiophenyl]-2-morpholino-propene | 2 | Triglycidyl isocyanurate | 15 | 1-Methoxy-propanol | 180 |
| 13 | K | 100 | Benzophenone | 3 | — | — | Methyl iso-butyl ketone | 100 |
| 14 | L | 100 | Benzoin ethyl ether | 1 | — | — | Isopropanol | 100 |
| 15 | L | 100 | Benzoin ethyl ether | 1 | CYMEL 301*3 | 10 | Isopropanol | 100 |

Note
*3 CYMEL 301 listed in Table 2 is a methylated melamine resin manufactured by Mitsui Cyanamide Co., Ltd.

Test Examples 8–15

Each of the photopolymerizable compositions obtained in Examples 8 to 15 was applied to various substrates to a thickness of 0.5 to 0.7 μm when dried and irradiated for curing with a mercury lamp at a dose of mj/cm² at a distance of 30 cm therefrom in a nitrogen gas stream.

The coating was further coated with an aminoalkyd coating composition (AMILAC No.1000, product of Kansai Paint Co., Ltd.) to a thickness of 25 μm when dried and heated at 140° C. for 20 minutes for curing. The test panels thus prepared were subjected to a salt spray test, filiform corrosion test and outdoor exposure test by the same methods already described. Table 3 shows the results.

Table 3 given below shows that the photopolymerizable compositions of the invention impart high corrosion resistance to various substrates when applied thereto.

TABLE 3

| Example No. | 8 | 9 | 10 | 11 | 12 | 13 | 14 | 15 |
|---|---|---|---|---|---|---|---|---|
| Substrate, test item | | | | | | | | |
| Zn-plated steel panel | | | | | | | | |
| SST (mm) | 1.3 | 1.0 | 1.5 | 0.8 | 0.6 | 0.8 | 0.8 | 0.6 |
| FCT (mm) | 0.7 | 0.8 | 1.1 | 0.5 | 0.6 | 0.1 | 1.0 | 1.1 |
| EPT (mm) | 1.2 | 0.8 | 0.8 | 0.5 | 0.3 | 0.3 | 0.8 | 0.8 |
| Cold-rolled steel panel | | | | | | | | |
| SST (mm) | 2.5 | 2.2 | 2.6 | 1.0 | 0.8 | 1.2 | 1.2 | 1.0 |
| FCT (mm) | 1.6 | 1.1 | 1.5 | 0.8 | 0.8 | 0.3 | 1.3 | 1.2 |
| EPT (mm) | 1.7 | 1.2 | 1.3 | 0.6 | 0.3 | 0.6 | 1.1 | 1.0 |
| Sn-plated steel panel | | | | | | | | |
| SST (mm) | 0.8 | 0.6 | 1.0 | 0.6 | 0.3 | 0.8 | 1.0 | 0.7 |
| FCT (mm) | 0.6 | 0.3 | 0.8 | 0.3 | 0.2 | 0.1 | 0.8 | 0.6 |
| EPT (mm) | 1.0 | 0.8 | 1.2 | 0.3 | 0.1 | 0.1 | 0.4 | 0.3 |
| Cr-plated steel panel | | | | | | | | |
| SST (mm) | 0.8 | 0.6 | 1.2 | 0.3 | 0.2 | 0.4 | 0.6 | 0.5 |
| FCT (mm) | 0.5 | 0.3 | 0.7 | 0.2 | 0.0 | 0.0 | 0.5 | 0.3 |
| EPT (mm) | 0.5 | 0.2 | 0.6 | 0.2 | 0.1 | 0.0 | 0.4 | 0.4 |
| SUS 304 | | | | | | | | |
| SST (mm) | 0.2 | 0.0 | 0.3 | 0.0 | 0.0 | 0.0 | 0.3 | 0.0 |
| FCT (mm) | 0.2 | 0.0 | 0.2 | 0.0 | 0.0 | 0.0 | 0.1 | 0.0 |
| EPT (mm) | 0.1 | 0.0 | 0.2 | 0.0 | 0.0 | 0.0 | 0.2 | 0.0 |
| Al panel | | | | | | | | |
| SST (mm) | 0.5 | 0.3 | 0.5 | 0.2 | 0.1 | 0.6 | 0.5 | 0.3 |
| FCT (mm) | 0.7 | 0.5 | 0.8 | 0.3 | 0.0 | 0.1 | 0.1 | 0.3 |
| EPT (mm) | 0.3 | 0.2 | 1.0 | 0.5 | 0.7 | 0.2 | 0.2 | 0.1 |

We claim:

1. A corrosion preventive resin characterized in that the resin has in the molecule group selected from among the groups represented by the general formula

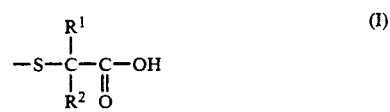

(I)

wherein $R^1$ and $R^2$ are the same or different and are each a hydrogen atom or alkyl having 1 to 8 carbon atoms, and groups represented by the general formula

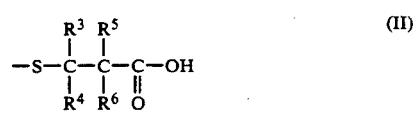

(II)

wherein $R^3$, $R^4$, $R^5$ and $R^6$ are the same or different and are each a hydrogen atom, alkyl having 1 to 8 carbon atoms or a group forming a bivalent o-phenylene group along with two carbon atoms attached thereto at least one chelate forming group represented by the formula

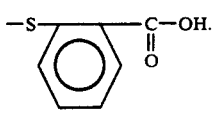

2. A resin as defined in claim 1 which has a number average molecular weight of about 570 to about 10000.

3. A resin as defined in claim 1 which has 1 to 300 chelate forming groups per molecule.

4. A resin composition comprising a resin as defined in claim 1 and a crosslinking agent admixed therewith.

5. A photopolymerizable composition characterized in that the composition consists essentially of:

(a) a resin having in the molecule at least one mole of polymerizable double bond per 1000 g of the resin and at least one chelate forming group, per molecule, selected from among groups represented by the general formula

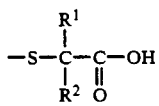
(I)

wherein $R^1$ and $R^2$ are the same or different and are each a hydrogen atom or alkyl having 1 to 8 carbon atoms, and groups represented by the general formula

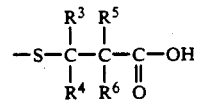
(II)

wherein $R^3$, $R^4$, $R^5$ and $R^6$ are the same or different and are each a hydrogen atom, alkyl having 1 to 8 carbon atoms or a group forming a bivalent o-phenylene group along with two carbon atoms attached thereto, and (b) a photopolymerization initiator.

6. A composition as defined in claim 5 wherein the resin (a) has a number average molecular weight of about 570 to about 100000.

7. A composition as defined in claim 5 which has 1 to 300 chelate forming groups per molecule.

8. A composition as defined in claim 5 which has 1.5 to 4.0 moles of polymerizable double bond per 1000 g of the resin.

9. A composition as defined in claim 5 further comprising a crosslinking agent.

10. A composition as defined in claim 5 wherein the photopolymerization initiator (b) is present in an amount of 0.1 to 20 parts by weight per 100 parts by weight of the resin (a).

* * * * *

UNITED STATES PATENT AND TRADEMARK OFFICE
CERTIFICATE OF CORRECTION

PATENT NO. : 5,196,487
DATED : March 23, 1993
INVENTOR(S) : Hideo KOGURE et al.

It is certified that error appears in the above-indentified patent and that said Letters Patent is hereby corrected as shown below:

Please correct Claim 1, Column 26, lines 38-58, as follows:

Col. 26, line 38, delete "group selected from among";
lines 39-57, delete in their entirety; and
line 58, delete "along with two carbon atoms attached thereto".

Signed and Sealed this

Nineteenth Day of April, 1994

Attest:

BRUCE LEHMAN

*Attesting Officer*  *Commissioner of Patents and Trademarks*